United States Patent
Kawahara (10) Patent No.: US 10,175,185 B2
(45) Date of Patent: Jan. 8, 2019

(54) METHODS FOR MANUFACTURING DOUBLY BENT X-RAY FOCUSING DEVICE, DOUBLY BENT X-RAY FOCUSING DEVICE ASSEMBLY, DOUBLY BENT X-RAY SPECTROSCOPIC DEVICE AND DOUBLY BENT X-RAY SPECTROSCOPIC DEVICE ASSEMBLY

(71) Applicant: RIGAKU CORPORATION, Tokyo (JP)

(72) Inventor: Naoki Kawahara, Takatsuki (JP)

(73) Assignee: Rigaku Corporation, Akishima-shi, Tokyo (JP)

( * ) Notice: Subject to any disclaimer, the term of this patent is extended or adjusted under 35 U.S.C. 154(b) by 0 days.

(21) Appl. No.: 15/712,799

(22) Filed: Sep. 22, 2017

(65) Prior Publication Data

US 2018/0011035 A1   Jan. 11, 2018

Related U.S. Application Data

(63) Continuation of application No. PCT/JP2016/059266, filed on Mar. 23, 2016.

(30) Foreign Application Priority Data

Mar. 26, 2015   (JP) ................. 2015-063764

(51) Int. Cl.
   *G01N 23/22*   (2018.01)
   *G01N 23/223*   (2006.01)
   (Continued)

(52) U.S. Cl.
   CPC ......... *G01N 23/223* (2013.01); *G01N 23/207* (2013.01); *G01N 23/22* (2013.01);
   (Continued)

(58) Field of Classification Search
   CPC .......... G21K 1/06; G21K 1/062; G21K 1/067; G21K 2201/06; G21K 2201/061;
   (Continued)

(56) References Cited

U.S. PATENT DOCUMENTS 4,203,034 A * 5/1980 Carroll, Jr. ........... G01N 23/205
                                                          378/145
4,599,741 A * 7/1986 Wittry .................. G01N 23/223
                                                          378/45
(Continued)

FOREIGN PATENT DOCUMENTS

CN   103057122 A   4/2013
JP   63-236948 A   10/1988
(Continued)

OTHER PUBLICATIONS

Summary of Notification of Reason(s) for Rejection issued in JP 2015-063764 dated Oct. 11, 2016.
(Continued)

*Primary Examiner* — Allen C. Ho
(74) *Attorney, Agent, or Firm* — Sughrue Mion, PLLC (57) ABSTRACT

A doubly bent X-ray spectroscopic device (1) according to the present invention includes: a glass plate (3) which is deformed into a shape having a doubly bent surface by being sandwiched between a doubly curved convex surface (21*a*) of a convex forming die (21) and a doubly curved concave surface (22*a*), of a concave forming die (22), that matches the doubly curved convex surface (21*a*), and being heated to a temperature of 400° C. to 600° C.; and a reflection coating (5) configured to reflect X-rays, which is formed on a concave surface (3*a*) of the deformed glass plate (3).

6 Claims, 5 Drawing Sheets

(51) Int. Cl.
*G21K 1/06* (2006.01)
*G01N 23/207* (2018.01)

(52) U.S. Cl.
CPC .............. *G21K 1/06* (2013.01); *G21K 1/062* (2013.01); *G21K 1/067* (2013.01); *G01N 2223/315* (2013.01); *G21K 2201/06* (2013.01); *G21K 2201/061* (2013.01); *G21K 2201/062* (2013.01); *G21K 2201/064* (2013.01); *G21K 2201/067* (2013.01)

(58) Field of Classification Search
CPC ....... G21K 2201/062; G21K 2201/064; G21K 2201/067; G01N 23/207; G01N 23/2076; G01N 23/22; G01N 23/223; G01N 2223/315
USPC ................. 378/70, 71, 73, 82, 84, 44–46, 49
See application file for complete search history.

(56) References Cited

U.S. PATENT DOCUMENTS

| | | | | |
|---|---|---|---|---|
| 4,807,268 A * | 2/1989 | Wittry | G01N 23/223 | 378/82 |
| 4,828,598 A * | 5/1989 | Imamura | C03B 23/023 | 65/104 |
| 4,949,367 A * | 8/1990 | Huizing | G01N 23/2076 | 378/82 |
| 5,108,480 A * | 4/1992 | Sugiyama | C03B 23/0305 | 65/106 |
| 5,127,028 A * | 6/1992 | Wittry | G21K 1/06 | 378/81 |
| 5,164,975 A * | 11/1992 | Steinmeyer | G21K 1/06 | 378/145 |
| 5,383,990 A * | 1/1995 | Tsuji | B32B 17/10036 | 156/102 |
| 5,757,883 A * | 5/1998 | Haisma | B82Y 10/00 | 378/84 |
| 5,892,809 A * | 4/1999 | Wittry | G21K 1/06 | 378/45 |
| 5,923,720 A * | 7/1999 | Barton | B82Y 10/00 | 378/83 |
| 6,233,096 B1 * | 5/2001 | Marcelli | B82Y 10/00 | 359/569 |
| 6,236,710 B1 * | 5/2001 | Wittry | G21K 1/06 | 378/82 |
| 6,285,506 B1 * | 9/2001 | Chen | G21K 1/06 | 359/642 |
| 6,317,483 B1 * | 11/2001 | Chen | B82Y 10/00 | 378/145 |
| 6,333,961 B1 * | 12/2001 | Murakami | B82Y 10/00 | 378/34 |
| 6,381,303 B1 * | 4/2002 | Vu | G01N 23/20 | 378/46 |
| 6,498,830 B2 * | 12/2002 | Wittry | G21K 1/06 | 378/82 |
| 6,606,371 B2 * | 8/2003 | Antonell | G21K 1/06 | 378/84 |
| 6,680,996 B2 * | 1/2004 | Yokhin | G01N 23/20 | 378/70 |
| 6,697,454 B1 * | 2/2004 | Nicolich | G21K 1/06 | 378/48 |
| 6,816,570 B2 * | 11/2004 | Janik | G01N 23/20 | 378/50 |
| 6,829,327 B1 * | 12/2004 | Chen | G01N 23/223 | 378/44 |
| 6,931,097 B1 * | 8/2005 | Davis, Jr. | B82Y 10/00 | 378/37 |
| 6,934,359 B2 * | 8/2005 | Chen | B82Y 10/00 | 378/45 |
| 7,035,374 B2 * | 4/2006 | Chen | G21K 1/06 | 378/84 |
| 7,072,439 B2 * | 7/2006 | Radley | G01N 23/12 | 378/47 |
| 7,076,024 B2 * | 7/2006 | Yokhin | G01N 23/201 | 378/70 |
| 7,092,843 B2 * | 8/2006 | Moore | G01N 23/20 | 702/179 |
| 7,104,690 B2 * | 9/2006 | Radley | A61B 6/586 | 378/207 |
| 7,120,228 B2 * | 10/2006 | Yokhin | G01N 23/20008 | 378/90 |
| 7,206,375 B2 * | 4/2007 | Chen | G01N 23/02 | 378/51 |
| 7,248,670 B2 * | 7/2007 | Hoghoj | B82Y 10/00 | 378/145 |
| 7,257,193 B2 * | 8/2007 | Radley | H05G 1/36 | 378/108 |
| 7,277,527 B2 * | 10/2007 | Gallagher | G01N 23/223 | 250/432 R |
| 7,298,817 B2 * | 11/2007 | Chen | G01N 23/223 | 378/44 |
| 7,317,784 B2 * | 1/2008 | Durst | G01N 23/20 | 378/124 |
| 7,415,096 B2 * | 8/2008 | Sherman | G21K 1/06 | 378/70 |
| 7,440,541 B2 * | 10/2008 | Hubbard-Nelson | G01N 33/287 | 378/45 |
| 7,583,789 B1 * | 9/2009 | MacDonald | B82Y 10/00 | 378/70 |
| 7,590,220 B1 * | 9/2009 | Lee | G01N 23/2076 | 378/57 |
| 7,691,279 B2 * | 4/2010 | Koike | B24B 37/013 | 216/31 |
| 7,738,629 B2 * | 6/2010 | Chen | G21K 1/06 | 378/84 |
| 7,738,630 B2 * | 6/2010 | Burdett, Jr. | B82Y 10/00 | 378/84 |
| 7,763,820 B1 * | 7/2010 | Sommer, Jr. | B07C 5/342 | 209/576 |
| 7,899,154 B2 * | 3/2011 | Chen | G01N 23/223 | 378/45 |
| 7,933,383 B2 * | 4/2011 | Verman | B82Y 10/00 | 378/145 |
| 7,991,116 B2 * | 8/2011 | Chen | B82Y 10/00 | 250/503.1 |
| 8,050,382 B2 * | 11/2011 | Chen | G01N 23/223 | 378/47 |
| 8,058,621 B2 * | 11/2011 | Kommareddy | G01N 23/207 | 250/364 |
| 8,121,254 B2 | 2/2012 | Murakami et al. | | |
| 8,137,574 B2 * | 3/2012 | Otsuka | B24B 7/242 | 204/192.33 |
| 8,422,633 B2 * | 4/2013 | Lantz | G01N 23/20008 | 378/84 |
| 8,557,149 B2 * | 10/2013 | Maj | B29D 11/00557 | 264/1.32 |
| 8,559,597 B2 * | 10/2013 | Chen | G01N 23/223 | 378/85 |
| 8,824,631 B2 | 9/2014 | Mitsuda et al. | | |
| 8,855,809 B2 * | 10/2014 | Spencer | B07C 5/3416 | 378/53 |
| 9,008,271 B2 * | 4/2015 | Burshtein | G21K 1/046 | 378/84 |
| 9,063,066 B2 * | 6/2015 | Peterson | G01N 23/223 | |
| 9,240,254 B2 * | 1/2016 | Schueler | G21K 1/06 | |
| 9,335,280 B2 * | 5/2016 | Pomerantz | G01N 23/223 | |
| 9,348,217 B2 * | 5/2016 | Hamamoto | G03F 1/22 | |
| 9,375,900 B2 * | 6/2016 | Tsuchiya | C03B 23/0252 | |
| 9,383,326 B2 * | 7/2016 | Beumer | G01N 23/223 | |
| 9,449,780 B2 * | 9/2016 | Chen | H01J 35/08 | |
| 9,551,677 B2 * | 1/2017 | Mazor | G01N 23/223 | |
| 9,586,061 B2 * | 3/2017 | Burshtein | G21K 1/04 | |
| 9,594,036 B2 * | 3/2017 | Yun | G01N 23/223 | |
| 9,666,322 B2 * | 5/2017 | Mazor | G21K 1/06 | |
| 9,714,907 B2 * | 7/2017 | Matsushita | G01N 23/20 | |
| 9,720,316 B2 * | 8/2017 | Mikami | G03F 1/24 | |

(56) References Cited

U.S. PATENT DOCUMENTS

| | | | | |
|---|---|---|---|---|
| 9,726,969 | B2* | 8/2017 | Hamamoto | G03F 1/24 |
| 9,740,091 | B2* | 8/2017 | Onoue | G03F 1/24 |
| 9,746,762 | B2* | 8/2017 | Hamamoto | G03F 1/24 |
| 9,823,203 | B2* | 11/2017 | Yun | H01J 35/08 |
| 2001/0031034 | A1 | 10/2001 | Wittry | |
| 2010/0190113 | A1 | 7/2010 | Murakami et al. | |
| 2011/0110499 | A1 | 5/2011 | Mitsuda et al. | |

FOREIGN PATENT DOCUMENTS

| | | | | |
|---|---|---|---|---|
| JP | 08-201589 A | | 8/1996 | |
| JP | 08-201593 A | | 8/1996 | |
| JP | 2006-308487 A | | 11/2006 | |
| JP | 2007-285791 A | | 11/2007 | |
| JP | 2008-175755 A | | 7/2008 | |
| JP | 2011-117741 A | | 6/2011 | |
| JP | 6069609 B2 * | | 2/2017 | G21K 1/06 |
| WO | 2006/022333 A1 | | 3/2006 | |
| WO | 2008/090988 A1 | | 7/2008 | |
| WO | 2010/008086 A1 | | 1/2010 | |

OTHER PUBLICATIONS

Decision of Grant issued in JP 2015-063764 dated Nov. 15, 2016.
International Search Report of PCT/JP2016/059266 dated May 17, 2016.
Translation of International Preliminary Report on Patentability dated Oct. 5, 2017, in counterpart International Application No. PCT/JP2016/059266.
Communication dated Jul. 3, 2018, from the European Patent Office in counterpart European Application No. 16768843.1.
Markus Kramer, et al., "Design of a doubly-curved crystal to improve X-ray fluorescence analysis of aerosol particles", Spectrochimica Acta. Part B: Atomic Spectroscopy, New York, NY, US, US, vol. 63, No. 12, Dec. 1, 2008, pp. 1408-1414, XP02571626, (7 pages total).
Communication dated Apr. 3, 2018 from the State Intellectual Property Office of the P.R.C. In counterpart Application No. 201680018150.2.
Communication dated Jul. 19, 2018, in corresponding Chinese application No. 201680018150.2.
Liu June, "Research on the Micro-embossing of Infrared Glass", Chinese Master's Theses Full-text Database, 2011-4.

* cited by examiner

METHODS FOR MANUFACTURING DOUBLY BENT X-RAY FOCUSING DEVICE, DOUBLY BENT X-RAY FOCUSING DEVICE ASSEMBLY, DOUBLY BENT X-RAY SPECTROSCOPIC DEVICE AND DOUBLY BENT X-RAY SPECTROSCOPIC DEVICE ASSEMBLY

CROSS REFERENCE TO THE RELATED APPLICATION

This application is a continuation application, under 35 U.S.C. § 111(a), of international application No. PCT/JP2016/059266, filed Mar. 23, 2016, which claims priority to Japanese patent application No. 2015-063764, filed Mar. 26, 2015, the entire disclosure of which is herein incorporated by reference as a part of this application.

BACKGROUND OF THE INVENTION

Field of the Invention

The present invention relates to a doubly bent X-ray focusing device, a doubly bent X-ray spectroscopic device, apparatuses provided with the devices, and methods for manufacturing the devices.

Description of Related Art

Conventionally, a curved X-ray spectroscopic device has been known which has a concave shape in one direction or two directions, and is configured to focus and/or monochromate X-rays. In particular, in order to efficiently monochromate and focus X-rays, it is necessary to use a doubly curved X-ray spectroscopic device having a large spectroscopic surface that is concave in two directions. In this regard, deposition of a spectroscopic multilayer film on a substrate that has been machined into a predetermined doubly curved shape in advance is commonly performed. However, the substrate needs to have a surface roughness of several angstroms (several nm×10$^{-1}$) in root-mean-square roughness, and polishing of such a doubly-curved-shaped substrate requires advanced technology and much labor, which results in significant increase in cost, and limited application. Meanwhile, an X-ray spectroscopic device (Patent Documents 1 and 2) has been known in which a silicon single crystal plate member is anode-bonded to a substrate having a predetermined curved shape. In this case, however, the plate member needs to be elastically deformed, and therefore, the degree of freedom of the bent shape of the plate member after being deformed is low. Under such circumstances, there has been proposed a crystal lens (Patent Document 3) which is manufactured by increasing the temperature of a crystal plate of Si, Ge, or the like to a temperature near its melting point, and applying a load to the crystal plate by using predetermined concave and convex dies to thermoplastically deform the crystal plate.

RELATED DOCUMENT

Patent Document

[Patent Document 1] JP Laid-open Patent Publication No. H8-201589

[Patent Document 2] JP Laid-open Patent Publication No. H8-201593

[Patent Document 3] WO 2006/022333

However, in the crystal lens manufacturing method disclosed in Patent Document 3, special equipment is required for performing the pressurizing deformation at high temperature. Further, not only the macro-shape of the forming die but also the micro-shape of the forming die (the surface roughness of the forming die) that adversely affects X-ray reflection characteristics are transferred onto the formed product. Therefore, even when an X-ray reflection coating or a synthetic multilayer is formed on the formed product, desired performance cannot be obtained.

SUMMARY OF THE INVENTION

The present invention is made in view of the problem of the conventional art, and an object of the present invention is to provide a doubly bent X-ray focusing device, a doubly bent X-ray spectroscopic device, apparatuses provided with the devices, and easy and inexpensive methods for manufacturing the devices, in which a glass plate is not adversely affected by the surface roughness of a doubly curved convex surface of a convex forming die even when being heated and deformed by forming dies, and has a surface roughness equivalent to that of the glass plate before being heated and deformed, and a film is formed on a concave surface of the deformed glass plate, whereby excellent focusing performance and/or spectroscopic performance are achieved.

In order to attain the aforementioned object, a doubly bent X-ray focusing device according to a first aspect of the present invention, includes: a glass plate which is deformed into a shape having a doubly bent surface by being sandwiched between a doubly curved convex surface of a convex forming die and a doubly curved concave surface, of a concave forming die, that matches the doubly curved convex surface, and being heated to a temperature of 400° C. to 600° C.; and a reflection coating configured to reflect X-rays, the reflection coating being formed on a concave surface of the deformed glass plate.

According to the doubly bent X-ray focusing device of the first aspect, the glass plate is sandwiched between the doubly curved convex surface and the doubly curved concave surface that matches the doubly curved convex surface, and heated to a temperature of 400° C. to 600° C. to be deformed to the shape having the doubly bent surface. As a result, the glass plate is not adversely affected by the surface roughness of the doubly curved convex surface of the convex forming die, and has a surface roughness equivalent to that of the glass plate before being heated and deformed. Since the reflection coating is formed on the concave surface of the glass plate, excellent focusing performance is achieved.

A doubly bent X-ray focusing device assembly according to a second aspect of the present invention includes: the doubly bent X-ray focusing device of the first aspect; and a base to which the doubly bent X-ray focusing device is fixed.

According to the doubly bent X-ray focusing device assembly of the second aspect, since the assembly includes the doubly bent X-ray focusing device of the first aspect, the same effect as that of the doubly bent X-ray focusing device of the first aspect can be achieved.

A doubly bent X-ray spectroscopic device according to a third aspect of the present invention includes: a glass plate which is deformed into a shape having a doubly bent surface by being sandwiched between a doubly curved convex surface of a convex forming die and a doubly curved concave surface, of a concave forming die, that matches the doubly curved convex surface, and being heated to a temperature of 400° C. to 600° C.; and a synthetic multilayer configured to monochromate X-rays, the synthetic multilayer being formed on a concave surface of the deformed glass plate.

According to the doubly bent X-ray spectroscopic device of the third aspect, the glass plate is sandwiched between the doubly curved convex surface and the doubly curved concave surface that matches the doubly curved convex surface, and heated to a temperature of 400° C. to 600° C. to be deformed to the shape having the doubly bent surface. As a result, the glass plate is not adversely affected by the surface roughness of the doubly curved convex surface of the convex forming die, and has a surface roughness equivalent to that of the glass plate before being heated and deformed. Since the synthetic multilayer is formed on the concave surface of the glass plate, excellent focusing performance and spectroscopic performance are achieved.

A doubly bent X-ray spectroscopic device assembly according to a fourth aspect of the present invention includes: the doubly bent X-ray spectroscopic device of the third aspect; and a base to which the doubly bent X-ray spectroscopic device is fixed.

According to the doubly bent X-ray spectroscopic device assembly of the fourth aspect, since the assembly includes the doubly bent X-ray spectroscopic device of the third aspect, the same effect as that of the doubly bent X-ray spectroscopic device of the third aspect can be achieved.

An X-ray analyzing apparatus according to a fifth aspect of the present invention includes at least one of the doubly bent X-ray focusing device of the first aspect, the doubly bent X-ray focusing device assembly of the second aspect, the doubly bent X-ray spectroscopic device of the third aspect, and the doubly bent X-ray spectroscopic device assembly of the fourth aspect.

According to the X-ray analyzing apparatus of the fifth aspect, the apparatus includes at least one of the doubly bent X-ray focusing device of the first aspect, the doubly bent X-ray focusing device assembly of the second aspect, the doubly bent X-ray spectroscopic device of the third aspect, and the doubly bent X-ray spectroscopic device assembly of the fourth aspect. Therefore, the X-ray analyzing apparatus can perform accurate measurement while ensuring satisfactory focusing performance and/or spectroscopic performance.

A method for manufacturing a doubly bent X-ray focusing device according to a sixth aspect of the present invention, includes the steps of: preparing a glass plate having a surface roughness not more than 0.5 nm in root-mean-square roughness; preparing a convex forming die having a doubly curved convex surface; preparing a concave forming die having a doubly curved concave surface that matches the doubly curved convex surface; deforming the glass plate into a shape having a doubly bent surface by sandwiching the glass plate between the doubly curved convex surface of the convex forming die and the doubly curved concave surface of the concave forming die, and heating the glass plate to a temperature of 400° C. to 600° C.; and forming a reflection coating that reflects X-rays, on a concave surface of the deformed glass plate.

According to the manufacturing method of the sixth aspect, since the reflection coating is formed on the concave surface of the glass plate that is not adversely affected by the surface roughness of the doubly curved convex surface of the convex forming die even when being heated and deformed by the forming dies, and that has a surface roughness equivalent to that of the glass plate before being heated and deformed, it is possible to easily and inexpensively manufacture the doubly bent X-ray focusing device having excellent focusing performance.

A method for manufacturing a doubly bent X-ray focusing device assembly according to a seventh aspect of the present invention, includes the steps of: preparing a doubly bent X-ray focusing device manufactured by the manufacturing method as the sixth aspect; preparing a base to which the doubly bent X-ray focusing device is to be fixed; and fixing the doubly bent X-ray focusing device to the base.

According to the manufacturing method of the seventh aspect, since the doubly bent X-ray focusing device manufactured by the manufacturing method of the sixth aspect is fixed to the base, it is possible to easily and inexpensively manufacture the doubly bent X-ray focusing device assembly having excellent focusing performance.

A method for manufacturing a doubly bent X-ray focusing device assembly according to an eighth aspect of the present invention, includes the steps of: preparing a glass plate having a surface roughness not more than 0.5 nm in root-mean-square roughness; preparing a convex forming die having a doubly curved convex surface; preparing a concave forming die having a doubly curved concave surface that matches the doubly curved convex surface; deforming the glass plate into a shape having a doubly bent surface by sandwiching the glass plate between the doubly curved convex surface of the convex forming die and the doubly curved concave surface of the concave forming die, and heating the glass plate to a temperature of 400° C. to 600° C.; preparing a base to which the deformed glass plate is to be fixed; fixing the deformed glass plate to the base; and forming a reflection coating that reflects X-rays, on a concave surface of the glass plate fixed to the base.

According to the manufacturing method of the eighth aspect, since the reflection coating is formed on the concave surface of the glass plate that is not adversely affected by the surface roughness of the doubly curved convex surface of the convex forming die even when being heated and deformed by the forming dies, and that has a surface roughness equivalent to that of the glass plate before being heated and deformed, it is possible to easily and inexpensively manufacture the doubly bent X-ray focusing device assembly having excellent focusing performance.

A method for manufacturing a doubly bent X-ray spectroscopic device according to a ninth aspect of the present invention, includes the steps of: preparing a glass plate having a surface roughness not more than 0.5 nm in root-mean-square roughness; preparing a convex forming die having a doubly curved convex surface; preparing a concave forming die having a doubly curved concave surface that matches the doubly curved convex surface; deforming the glass plate into a shape having a doubly bent surface by sandwiching the glass plate between the doubly curved convex surface of the convex forming die and the doubly curved concave surface of the concave forming die, and heating the glass plate to a temperature of 400° C. to 600° C.; and forming a synthetic multilayer that monochromates X-rays, on a concave surface of the deformed glass plate.

According to the manufacturing method of the ninth aspect, since the synthetic multilayer is formed on the concave surface of the glass plate that is not adversely affected by the surface roughness of the doubly curved convex surface of the convex forming die even when being heated and deformed by the forming dies, and that has a surface roughness equivalent to that of the glass plate before being heated and deformed, it is possible to easily and inexpensively manufacture the doubly bent X-ray spectroscopic device having excellent focusing performance and spectroscopic performance.

A method for manufacturing a doubly bent X-ray spectroscopic device assembly according to a tenth aspect of the present invention, includes the steps of: preparing a doubly bent X-ray spectroscopic device manufactured by the manufacturing method of the ninth aspect; preparing a base to which the doubly bent X-ray spectroscopic device is to be fixed; and fixing the doubly bent X-ray spectroscopic device to the base.

According to the manufacturing method of the tenth aspect, since the doubly bent X-ray spectroscopic device manufactured by the manufacturing method of the ninth aspect is fixed to the base, it is possible to easily and inexpensively manufacture the doubly bent X-ray spectroscopic device assembly having excellent focusing performance and spectroscopic performance.

A method for manufacturing a doubly bent X-ray spectroscopic device assembly according to an eleventh aspect of the present invention, includes the steps of: preparing a glass plate having a surface roughness not more than 0.5 nm in root-mean-square roughness; preparing a convex forming die having a doubly curved convex surface; preparing a concave forming die having a doubly curved concave surface that matches the doubly curved convex surface; deforming the glass plate into a shape having a doubly bent surface by sandwiching the glass plate between the doubly curved convex surface of the convex forming die and the doubly curved concave surface of the concave forming die, and heating the glass plate to a temperature of 400° C. to 600° C.; preparing a base to which the deformed glass plate is to be fixed; fixing the deformed glass plate to the base; and forming a synthetic multilayer that monochromates X-rays, on a concave surface of the glass plate fixed to the base.

According to the manufacturing method of the eleventh aspect, since the synthetic multilayer is formed on the concave surface of the glass plate that is not adversely affected by the surface roughness of the doubly curved convex surface of the convex forming die even when being heated and deformed by the forming dies, and that has a surface roughness equivalent to that of the glass plate before being heated and deformed, it is possible to easily and inexpensively manufacture the doubly bent X-ray spectroscopic device assembly having excellent focusing performance and spectroscopic performance.

Any combination of at least two constructions, disclosed in the appended claims and/or the specification and/or the accompanying drawings should be construed as included within the scope of the present invention. In particular, any combination of two or more of the appended claims should be equally construed as included within the scope of the present invention.

BRIEF DESCRIPTION OF THE DRAWINGS

In any event, the present invention will become more clearly understood from the following description of preferred embodiments thereof, when taken in conjunction with the accompanying drawings. However, the embodiments and the drawings are given only for the purpose of illustration and explanation, and are not to be taken as limiting the scope of the present invention in any way whatsoever, which scope is to be determined by the appended claims. In the accompanying drawings, like reference numerals are used to denote like parts throughout the several views, and:

DESCRIPTION OF EMBODIMENTS

Hereinafter, a doubly bent X-ray focusing device 1 according to a first embodiment of the present invention will be described. The doubly bent X-ray focusing device 1 of the first embodiment shown in FIG. 1 includes: a glass plate 3 which is deformed into a shape having a doubly bent surface by being sandwiched between a doubly curved convex surface of a convex forming die and a doubly curved concave surface, of a concave forming die, that matches the doubly curved convex surface, and being heated to a temperature of 400° C. to 600° C., for example, 500° C.; and a reflection coating 5 of Au (gold) which is formed on a concave surface 3a of the deformed glass plate 3 by, for example, vacuum deposition, and is configured to reflect X-rays. Although the doubly bent surface is a toroidal surface (annular side surface) in the doubly bent X-ray focusing device 1 of the present embodiment, the doubly bend surface of the present invention is not limited to the toroidal surface, and may be an ellipsoid of revolution, a logarithmic spiral surface of revolution, or the like.

Figure 1:
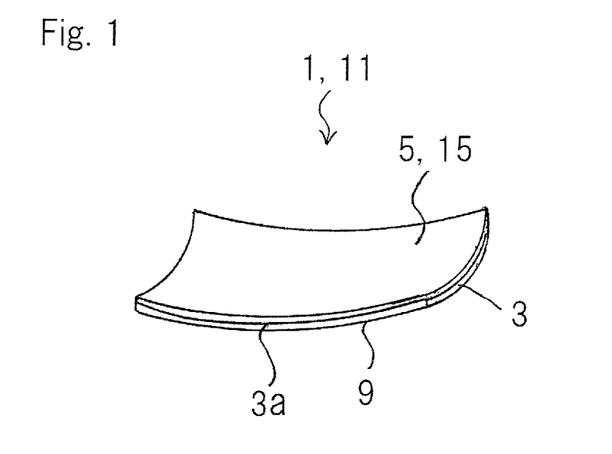
FIG. 1 is a schematic diagram showing a doubly bent X-ray focusing device according to a first embodiment of the present invention, or a doubly bent X-ray spectroscopic device according to a third embodiment of the present invention.

When the heating temperature to deform the glass plate 3 is less than 400° C., the glass plate 3 may sometimes not be formed to have a desired doubly bent surface even if the time for the heating and deformation is increased. On the other hand, when the heating temperature exceeds 600° C., although the time required for the heating and deformation is reduced, there is a risk that the surface roughness of the convex surface of the convex forming die may be transferred to the concave surface 3a of the glass plate 3. Therefore, the heating temperature to deform the glass plate 3 is preferably 400° C. to 600° C., and more preferably 450° C. to 550° C.

The blank glass plate 3, which has not been deformed, has a surface roughness not more than 0.5 nm in root-mean-square roughness. The blank glass plate 3 is, for example, a cover glass for microscopic observation or for a display of electronic equipment, and specifically is a rectangle plate made of borosilicate glass and having a long side of 75 mm, a short side of 25 mm, and a thickness of 0.15 mm. The thickness of the blank glass plate 3 is preferably not more than 1 mm because the thinner the blank glass plate 3 is, the more rapidly the blank glass plate 3 is heated and deformed, which facilitates forming. The dimension, shape, and material of the blank glass plate 3 may be other than those mentioned above as long as the surface roughness thereof is not more than 0.5 nm in root-mean-square roughness.

According to the doubly bent X-ray focusing device 1 of the first embodiment, the blank glass plate 3 is sandwiched between the doubly curved convex surface and the doubly curved concave surface that matches the doubly curved convex surface and is heated to a temperature of 400° C. to 600° C. to be deformed into the shape having the doubly bent surface. As a result, the glass plate 3 is not adversely affected by the surface roughness of the doubly curved convex surface 21a of the convex forming die 21 (FIG. 7), and has the surface roughness equivalent to that of the glass plate 3 before being heated and deformed. Since the reflection coating 5 is formed on the concave surface 3a of the glass plate 3, excellent focusing performance is achieved. Further, the deformed glass plate 3 can maintain its shape, that is, has a self-supporting shape. Therefore, only by forming the reflection coating 5 on the concave surface 3a of the glass plate 3, the glass plate 3 can be used as the doubly bent X-ray focusing device 1 that can be handled as it is.

Next, a doubly bent X-ray focusing device assembly 6 according to a second embodiment of the present invention will be described. A doubly bent X-ray focusing device assembly 6 of the second embodiment shown in FIG. 2 includes the doubly bent X-ray focusing device 1 of the first embodiment, and a base 7 to which the doubly bent X-ray focusing device 1 is fixed. The base 7 is a concave stainless-steel base having a doubly curved concave surface 7a identical to the doubly curved concave surface of the concave forming die. A convex surface 9 of the doubly bent X-ray focusing device 1 (the convex surface of the glass plate 3) is fixed to the doubly curved concave surface 7a of the base 7 by means of an adhesive.

Figure 2:
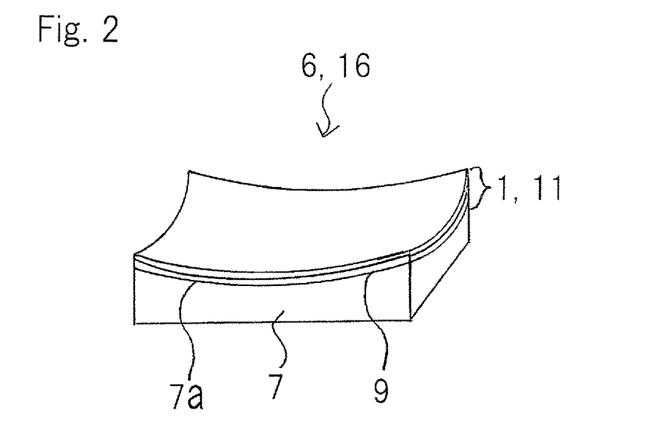
FIG. 2 is a schematic diagram showing a doubly bent X-ray focusing device assembly according to a second embodiment of the present invention, or a doubly bent X-ray spectroscopic device assembly according to a fourth embodiment of the present invention.
Figure 3:
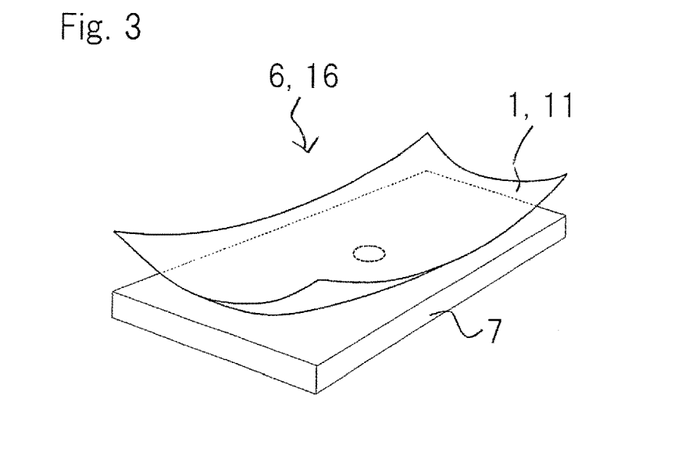
FIG. 3 is a schematic diagram showing a doubly bent X-ray focusing device assembly according to a modification of the second embodiment of the present invention, or a doubly bent X-ray spectroscopic device assembly according to a modification of the fourth embodiment of the present invention.
Figure 4:
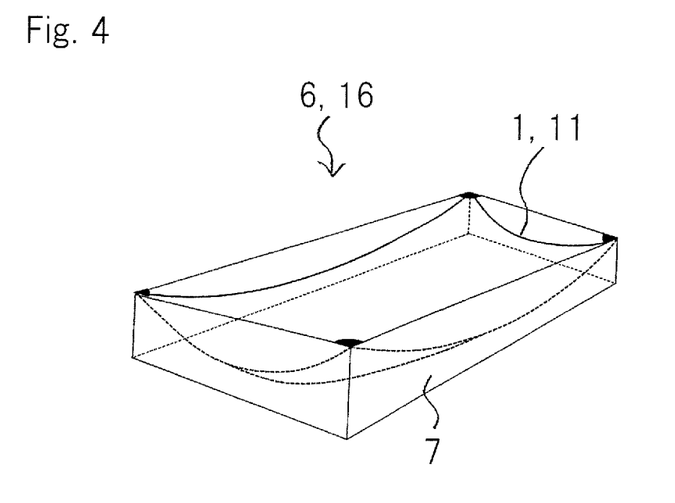
FIG. 4 is a schematic diagram showing a doubly bent X-ray focusing device assembly according to another modification of the second embodiment of the present invention, or a doubly bent X-ray spectroscopic device assembly according to another modification of the fourth embodiment of the present invention.

Since the doubly bent X-ray focusing device 1 has the self-supporting shape, it is sufficient that the base 7 is a fixture member to which the doubly bent X-ray focusing device 1 can be fixed, and the surface roughness of the double curved concave surface 7a of the base 7 may be inferior to the surface roughness of the glass plate 3. The base 7 is not limited to the concave base 7 as shown in FIG. 2, and may be a plate-shaped base 7 as shown in FIG. 3 or a box-shaped base 7 as shown in FIG. 4. That is, as in a modification shown in FIG. 3, the doubly bent X-ray focusing device assembly 6 may be configured such that a center portion of the convex surface 9 of the doubly bent X-ray focusing device 1 is fixed to a center portion of the plate-shaped base 7 by means of an elastic adhesive. Alternatively, as in another modification shown in FIG. 4, the doubly bent X-ray focusing device assembly 6 may be configured such that the four corners of the convex surface 9 of the doubly bent X-ray focusing device 1 are fixed to the four corners of the box-shaped base 7 by means of an elastic adhesive. The base 7 of the doubly bent X-ray focusing device assembly 6 is not limited to the bases 7 having the shapes shown in FIG. 2 to FIG. 4, and may be a frame-shaped base 7, or a base 7 having a square hole or a round hole, to which only the periphery of the doubly bent X-ray focusing device 1 is fixed. In these modifications, shape machining of the base 7 can be easily performed. In addition, even when there is a large temperature change, the difference in thermal expansion coefficient between the base 7 and the glass plate 3 hardly causes deformation, resulting in a high degree of freedom in selecting the material of the base 7.

Since the doubly bent X-ray focusing device assembly 6 of the second embodiment includes the doubly bent X-ray focusing device 1 of the first embodiment, the same effect as that of the doubly bent X-ray focusing device 1 of the first embodiment can be achieved.

Next, a doubly bent X-ray spectroscopic device according to a third embodiment of the present invention will be described. The doubly bent X-ray spectroscopic device 11 of the third embodiment shown in FIG. 1 is different from the doubly bent X-ray focusing device 1 of the first embodiment only in that a synthetic multilayer 15 is formed instead of the reflection coating 5 of the first embodiment, and other components thereof are the same as those of the first embodiment. That is, the synthetic multilayer 15 which monochromates X-rays, for example, a synthetic multilayer for C-Kα line that efficiently monochromates C-Kα line, is formed on the concave surface 3a of the glass plate 3 deformed into a shape having a doubly bent surface.

According to the doubly bent X-ray spectroscopic device 11 of the third embodiment, like the doubly bent X-ray focusing device 1 of the first embodiment, the glass plate 3 is not adversely affected by the surface roughness of the doubly curved convex surface 21a of the convex forming die 21 (FIG. 7), and has the surface roughness equivalent to that of the glass plate 3 before being heated and deformed. Since the synthetic multilayer 15 is formed on the concave surface 3a of the glass plate 3, excellent focusing performance and spectroscopic performance are achieved. Further, the deformed glass plate 3 can maintain its shape, that is, has a self-supporting shape. Therefore, only by forming the synthetic multilayer 15 on the concave surface 3a of the glass plate 3, the glass plate 3 can be used as the doubly bent X-ray focusing device 1 that can be handled as it is.

Next, a doubly bent X-ray spectroscopic device assembly 16 according to a fourth embodiment of the present invention will be described. The doubly bent X-ray spectroscopic device assembly 16 of the fourth embodiment shown in FIG. 2 includes the doubly bent X-ray spectroscopic device 11 of the third embodiment, and a base 7 to which the doubly bent X-ray spectroscopic device 11 is fixed. The base 7 is the same as the base 7 of the doubly bent X-ray focusing device assembly 6 of the second embodiment.

Since the doubly bent X-ray spectroscopic device assembly 16 of the fourth embodiment includes the doubly bent X-ray spectroscopic device 11 of the third embodiment, the same effect as that of the doubly bent X-ray spectroscopic device 11 of the third embodiment can be achieved.

Figure 5:
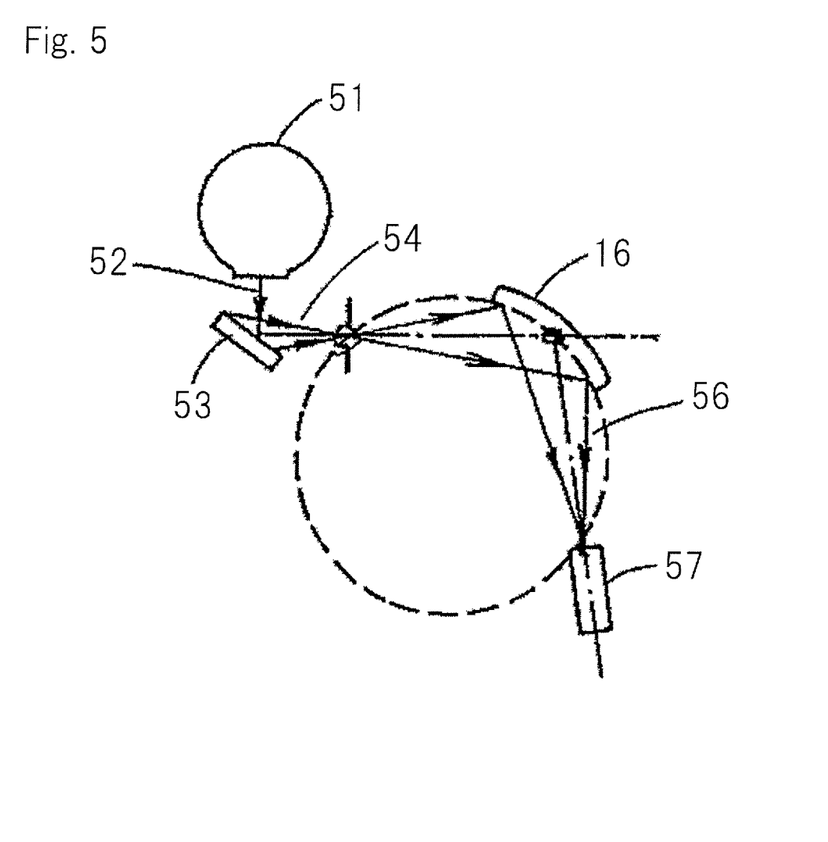
FIG. 5 is a schematic diagram showing an X-ray analyzing apparatus according to a fifth embodiment of the present invention.

Next, an X-ray analyzing apparatus according to a fifth embodiment of the present invention will be described. This X-ray analyzing apparatus is an X-ray fluorescence spectrometer, and includes the doubly bent X-ray spectroscopic device assembly 16 of the fourth embodiment. As shown in FIG. 5, the X-ray analyzing apparatus includes: an X-ray source 51 which irradiates a sample 53 with primary X-rays 52; the doubly bent X-ray spectroscopic device assembly 16 which monochromates fluorescent X-rays 54 generated from the sample 53; and an X-ray detector 57 which detects fluorescent X-rays 56 that have been monochromated and focused by the doubly bent X-ray spectroscopic device assembly 16. The X-ray analyzing apparatus performs quantitative analysis and/or qualitative analysis on the basis of detected intensity of the fluorescent X-rays.

Although the X-ray analyzing apparatus according to the fifth embodiment has been described as the X-ray fluorescence spectrometer provided with the doubly bent X-ray spectroscopic device assembly 16 of the fourth embodiment, the X-ray analyzing apparatus may be provided with at least one of: the doubly bent X-ray focusing device 1 of the first embodiment; the doubly bent X-ray focusing device assembly 6 of the second embodiment; the doubly bent X-ray spectroscopic device 11 of the third embodiment; and the doubly bent X-ray spectroscopic device assembly 16 of the fourth embodiment, or may be an X-ray analyzing apparatus other than X-ray fluorescence spectrometers.

Since the X-ray analyzing apparatus of the fifth embodiment is provided with at least one of: the doubly bent X-ray focusing device 1 of the first embodiment; the doubly bent X-ray focusing device assembly 6 of the second embodiment; the doubly bent X-ray spectroscopic device 11 of the third embodiment; and the doubly bent X-ray spectroscopic device assembly 16 of the fourth embodiment, the X-ray analyzing apparatus can perform highly accurate measurement while ensuring satisfactory focusing performance and/or spectroscopic performance.

Figure 6:
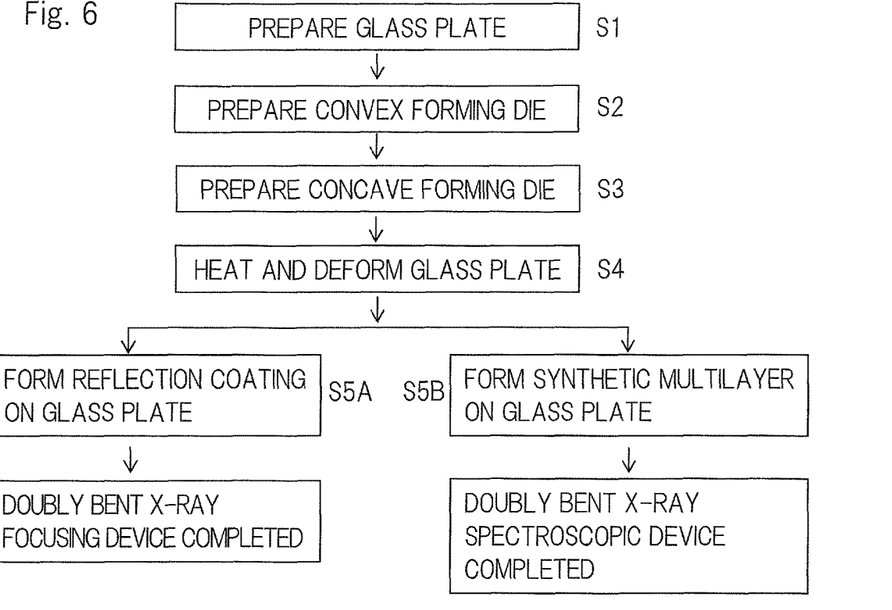
FIG. 6 is a diagram showing process steps of a doubly bent X-ray focusing device manufacturing method according to a sixth embodiment of the present invention, or process steps of a doubly bent X-ray spectroscopic device manufacturing method according to a ninth embodiment of the present invention.

Next, a method for manufacturing the doubly bent X-ray focusing device 1 according to a sixth embodiment of the present invention will be described. As shown in FIG. 6, this manufacturing method includes: step S1 of preparing the glass plate 3 having a surface roughness not more than 0.5 nm in root-mean-square roughness; step S2 of preparing the convex forming die 21 having the doubly curved convex surface 21a; step S3 of preparing the concave forming die 22 having the doubly curved concave surface 22a which matches the doubly curved convex surface 21a; step S4 of deforming the glass plate 3 into the shape having the doubly bent surface by sandwiching the glass plate 3 between the doubly curved convex surface 21a of the convex forming die 21 and the doubly curved concave surface 22a of the concave forming die 22, and heating the glass plate 3 to a temperature of 400° C. to 600° C.; and step S5A (step on the left side in FIG. 6) of forming the reflection coating 5 which reflects X-rays, on the concave surface of the deformed glass plate 3. Hereinafter, the manufacturing method will be described in order of the process steps.

In step S1, the glass plate 3 having the surface roughness not more than 0.5 nm in root-mean-square roughness is prepared. The blank glass plate 3 is, for example, a cover glass for microscopic observation or for a display of electronic equipment, and specifically, is a rectangle plate made of borosilicate glass and having a long side of 75 mm, a short side of 25 mm, and a thickness of 0.15 mm. The thickness of the blank glass plate 3 is preferably not more than 1 mm because the thinner the blank glass plate 3 is, the more rapidly the blank glass plate 3 is heated and deformed, which facilitates forming. The dimension, shape, and material of the blank glass plate 3 may be other than those mentioned above as long as the surface roughness thereof is not more than 0.5 nm in root-mean-square roughness.

In step S2, the convex forming die 21 having the desired doubly curved convex surface 21a is prepared. The doubly curved convex surface 21a of the convex forming die 21 is a toroidal surface in the manufacturing method of the present embodiment. The convex forming die 21 is made of stainless steel, and has a mass of 300 g. The doubly curved convex surface 21a has, in a plan view, a rectangular shape with a long side of 75 mm and a short side of 25 mm.

In step S3, the concave forming die 22 having the doubly curved concave surface 22a that matches the doubly curved convex surface 21a is prepared. The doubly curved concave surface 22a is a toroidal surface in the manufacturing method of the present embodiment. The concave forming die 22 is made of stainless steel. The doubly curved concave surface 22a of the concave forming die 22 has, in a plan view, a rectangular shape with a long side of 75 mm and a short side of 25 mm. The doubly curved concave surface 22a that matches the doubly curved convex surface 21a means the doubly curved concave surface 22a which is shifted from the doubly curved convex surface 21a by the thickness of the glass plate 3. The convex forming die 21 and the concave forming die 22 are machined dies, and the doubly curved convex surface 21a and the doubly curved concave surface 22a thereof are not subjected to special surface polishing. Therefore, these dies 21 and 22 are inferior in surface roughness to the blank glass plate 3.

Figure 7:
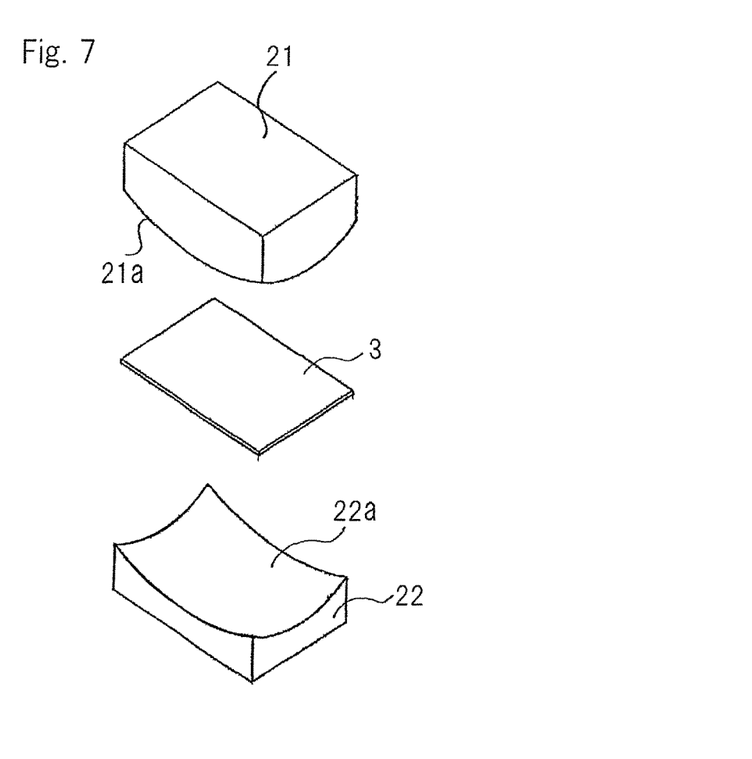
FIG. 7 is a diagram showing a process step of the doubly bent X-ray focusing device manufacturing method according to the sixth embodiment of the present invention, or a process step of the doubly bent X-ray spectroscopic device manufacturing method according to the ninth embodiment of the present invention.
Figure 8:
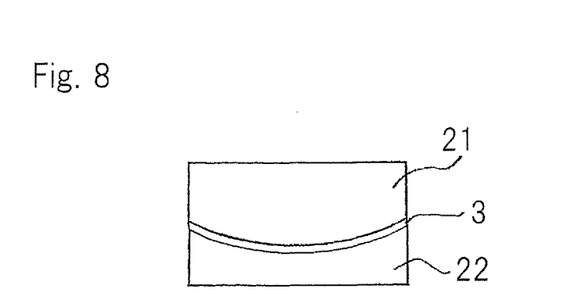
FIG. 8 is a diagram showing another process step of the doubly bent X-ray focusing device manufacturing method according to the sixth embodiment of the present invention, or another process step of the doubly bent X-ray spectroscopic device manufacturing method according to the ninth embodiment of the present invention.

In step S4, as shown in FIG. 7, the glass plate 3 is sandwiched between the doubly curved convex surface 21a of the convex forming die 21 and the doubly curved concave surface 22a of the concave forming die 22, and heated at 500° C. for 90 minutes, for example, whereby the glass plate 3 is thermoplastically deformed into a shape having the doubly bent surface only by the self-weight of the convex forming die 21 (FIG. 8). If the deformation due to the self-weight of the convex forming die 21 is not sufficient, a load may be applied from the top of the convex forming die 21. If the glass plate 3 is heated at a temperature less than 400° C., the glass plate 3 may sometimes not be formed into a shape having a desired doubly bent surface even if the heating time is increased or the load is increased. On the other hand, if the glass plate 3 is heated at a temperature exceeding 600° C., although the time required for deformation is reduced, there is a risk that the surface roughness of the doubly curved convex surface 21a of the convex forming die 21 is transferred to the concave surface 3a of the glass plate 3. Therefore, the heating temperature for deforming the glass plate 3 is preferably 400° C. to 600° C., and more preferably 450° C. to 550° C. Regarding heating equipment, special equipment for performing the pressurizing deformation at the high temperature is not required, and a simple and inexpensive electric furnace capable of heating the glass plate 3 at 400° C. to 600° C. suffices.

In step S5A of FIG. 6, after the deformed glass plate 3 is slowly cooled, the reflection coating 5 of Au (gold) that reflects X-rays is formed by, for example, vacuum deposition on the concave surface 3a of the deformed glass plate 3. Through the above-described process steps, the doubly bent X-ray focusing device 1 is manufactured. The deformed glass plate 3 can maintain its shape, that is, has a self-supporting shape. Therefore, only by forming the reflection coating 5 on the concave surface 3a of the glass plate 3, the glass plate 3 can be manufactured as the doubly bent X-ray focusing device 1 that can be handled as it is. Although the doubly bent surface is a toroidal surface (annular side surface) in the manufacturing method of the present embodiment, the doubly bend surface of the present invention is not limited to the toroidal surface, and may be an ellipsoid of revolution, a logarithmic spiral surface of revolution, or the like.

According to the manufacturing method of the sixth embodiment, the glass plate 3 is sandwiched between the doubly curved convex surface 21a and the doubly curved concave surface 22a that matches the doubly curved convex surface 21a, and heated to a temperature of 400° C. to 600° C. to be deformed into a shape having the doubly bent surface. As a result, even when the glass plate 3 is heated and deformed between the convex forming die 21 and the concave forming die 22, the glass plate 3 is not adversely affected by the surface roughness of the doubly curved convex surface 21a of the convex forming die 21, and has the surface roughness equivalent to that of the glass plate 3 before being heated and deformed. The reflection coating 5 is formed on the concave surface 3a of the glass plate 3. Therefore, it is possible to easily and inexpensively manufacture the doubly bent X-ray focusing device 1 having excellent focusing performance.

Figure 9:
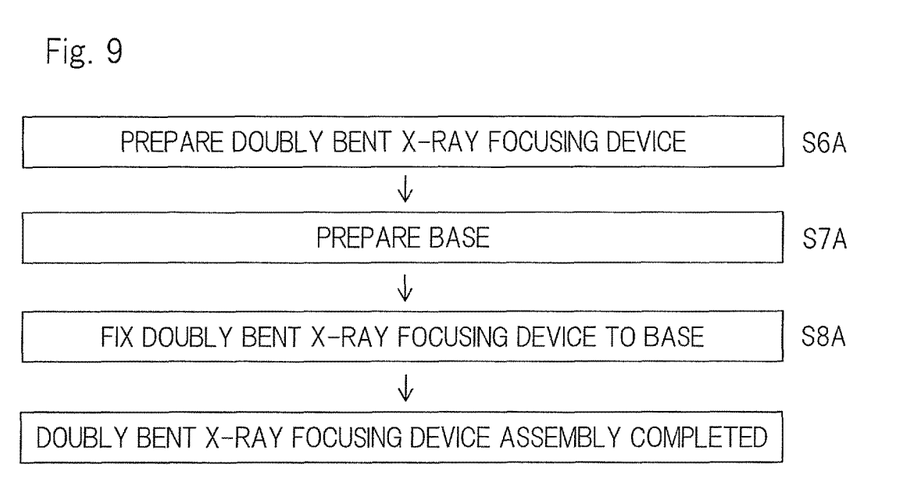
FIG. 9 is a diagram showing process steps of a doubly bent X-ray focusing device assembly manufacturing method according to a seventh embodiment of the present invention.

Next, a method for manufacturing the doubly bent X-ray focusing device assembly 6 according to a seventh embodiment of the present invention will be described. As shown in FIG. 9, this manufacturing method includes: step S6A of preparing the doubly bent X-ray focusing device 1 manufactured by the manufacturing method of the sixth embodiment; step S7A of preparing the base 7 to which the doubly bent X-ray focusing device 1 is to be fixed; and step S8A of fixing the doubly bent X-ray focusing device 1 to the base 7. Hereinafter, the manufacturing method will be described in order of the process steps.

In step S6A, the doubly bent X-ray focusing device 1 manufactured by the manufacturing method of the sixth embodiment is prepared.

In step S7A, the base 7 to which the doubly bent X-ray focusing device 1 is to be fixed is prepared. The same base 7 as that of the doubly bent X-ray focusing device assembly 6 of the second embodiment, for example, a concave stainless-steel base 7 having the same doubly curved concave surface 7a as the doubly curved concave surface 22a of the concave forming die 22, is prepared.

In step S8A, first, an adhesive, for example, epoxy resin, is applied to the entire concave surface 7a of the base 7 (FIG. 2). Next, the convex surface 9 of the doubly bent X-ray focusing device 1 (FIG. 2) is superposed on the concave surface 7a, of the base 7, to which the adhesive has been applied. Next, the convex surface 9 of the doubly bent X-ray focusing device 1 is adhered to the concave surface 7a of the base 7 while lightly pressing the doubly bent X-ray focusing device 1 with the doubly curved convex surface 21a of the convex forming die 21. Since the shape of the convex surface 9 of the doubly bent X-ray focusing device 1, which has the self-supporting shape, matches the shape of the concave surface 7a of the base 7, the doubly bent X-ray focusing device 1 is fixed to the base 7 without being deformed. Through the above-described process steps, the doubly bent X-ray spectroscopic device assembly 6 is manufactured.

According to the manufacturing method of the seventh embodiment, since the doubly bent X-ray focusing device 1 manufactured by the manufacturing method of the sixth embodiment is fixed to the base 7, it is possible to easily and inexpensively manufacture the doubly bent X-ray focusing device assembly 6 having excellent focusing performance.

Figure 10:
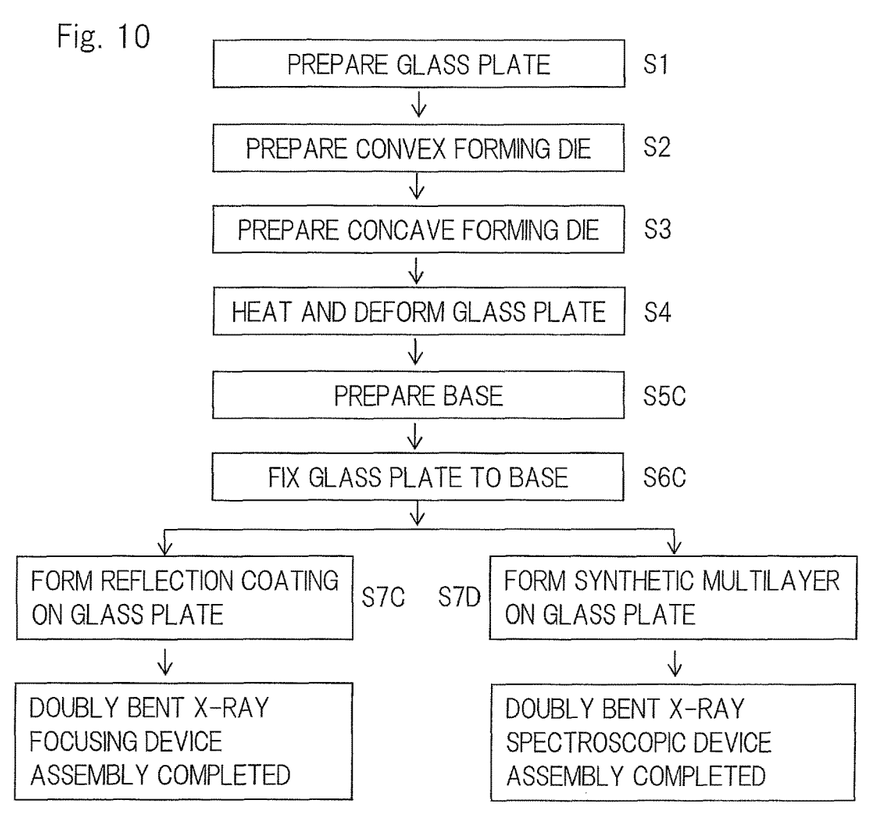
FIG. 10 is a diagram showing process steps of a doubly bent X-ray focusing device assembly manufacturing method according to an eighth embodiment of the present invention, or process steps of a doubly bent X-ray spectroscopic device assembly manufacturing method according to an eleventh embodiment of the present invention.

Next, a method for manufacturing a doubly bent X-ray focusing device assembly 6 according to an eighth embodiment of the present invention will be described. As shown in FIG. 10, this manufacturing method includes: step S1 of preparing the glass plate 3 having a surface roughness not more than 0.5 nm in root-mean-square roughness; step S2 of preparing the convex forming die 21 having the doubly curved convex surface 21a; step S3 of preparing the concave forming die 22 having the doubly curved concave surface 22a that matches the doubly curved convex surface 21a; step S4 deforming the glass plate 3 into a shape having the doubly bent surface by sandwiching the glass plate 3 between the doubly curved convex surface 21a of the convex forming die 21 and the doubly curved concave surface 22a of the concave forming die 22, and heating the glass plate 3 to a temperature of 400° C. to 600° C.; step S5C of preparing the base 7 to which the deformed glass plate 3 is to be fix; step S6C of fixing the deformed glass plate 3 to the base 7; and step S7C (step on the left side in FIG. 10) of forming the reflection coating 5 which reflects X-rays, on the concave surface 3a of the glass plate 3 fixed to the base 7. Hereinafter, the manufacturing method will be described in order of the process steps.

Steps S1 to S4 of the manufacturing method of the eighth embodiment are the same as steps S1 to S4 of the manufacturing method of the sixth embodiment, and the glass plate 3 is similarly heated and deformed.

In step S5C, the base 7 to which the deformed glass plate 3 is to be fixed is prepared. The same base 7 as that used in the manufacturing method of the seventh embodiment, for example, a concave stainless-steel base 7 having the same doubly curved concave surface 7a as the doubly curved concave surface 22a of the concave forming die 22, is prepared.

In step S6C, first, the convex forming die 21 and the deformed glass plate 3 are heated to a melting point of paraffin which is described later, and paraffin is applied to the convex surface 21a of the convex forming die 21, and then the concave surface 3a of the deformed glass plate 3 is superposed on the convex surface 21a having the paraffin. Then, the convex forming die 21 and the glass plate 3 are slowly cooled, whereby the glass plate 3 is held on the convex surface 21a of the convex forming die 21 due to the adhesion force of the paraffin. Next, an adhesive, for example, epoxy resin, is applied to the entire concave surface 7a of the base 7, and the convex surface 9 of the glass plate 3 adhered to and held by the convex surface 21a of the convex forming die 21 is superposed on and adhered to the concave surface 7a of the base 7, thereby fixing the glass plate 3 to the base 7.

After the deformed glass plate 3 is fixed, the entire structure, in which the convex forming die 21, the glass plate 3, and the base 7 are in the superposed state, is heated to the melting point of paraffin, whereby the convex forming die 21 is separated from the glass plate 3, and the paraffin remaining on the concave surface 3a of the glass plate 3 is removed. The paraffin used in this embodiment is desired to have a melting point at a low temperature that does not cause degradation of the adhesive, for example, 50° C. to 60° C.

In step S7C, the reflection coating 5 of Au (gold) that reflects X-rays is formed by, for example, vacuum deposition, on the concave surface 3a of the deformed glass plate 3 fixed to the base 7. Through the above-described process steps, the doubly bent X-ray focusing device assembly 6 is manufactured.

According to the manufacturing method of the eighth embodiment, as in the manufacturing method of the sixth embodiment, the glass plate 3 is sandwiched between the doubly curved convex surface 21a and the doubly curved concave surface 22a that matches the doubly curved convex surface 21a, and heated to a temperature of 400° C. to 600° C. to be deformed into a shape having the doubly bent surface. As a result, the glass plate 3 is not adversely affected by the surface roughness of the doubly curved convex surface 21a of the convex forming die 21, and has the surface roughness equivalent to that of the glass plate 3 before being heated and deformed. Then, the reflection coating 5 is formed on the concave surface 3a of the glass plate 3. Therefore, it is possible to easily and inexpensively manufacture the doubly bent X-ray focusing device assembly 6 having excellent focusing performance.

Next, a method for manufacturing a doubly bent X-ray spectroscopic device according to a ninth embodiment of the present invention will be described. This manufacturing method is different from the manufacturing method of the sixth embodiment only in that, as shown in FIG. 6, step S5B (step on the right side in FIG. 6) of forming the synthetic multilayer 15 that monochromates X-rays, on the concave surface 3a of the deformed glass plate 3 is included instead of step S5A of forming the reflection coating 5 that reflects X-rays, on the concave surface 3a of the deformed glass plate 3, and the other steps are the same as those of the sixth embodiment. The synthetic multilayer 15 which monochromates X-rays, for example, a synthetic multilayer 15 for C-Kα line, is formed on the concave surface 3a of the deformed glass plate 3, thereby to complete the doubly bent X-ray spectroscopic device 11. The deformed glass plate 3 can maintain its shape, that is, has a self-supporting shape. Therefore, only by forming the synthetic multilayer 15 on the concave surface 3a of the glass plate 3, the glass plate 3 can be manufactured as the doubly bent X-ray spectroscopic device 11 that can be handled as it is. Although the doubly bent surface is a toroidal surface (annular side surface) in the manufacturing method of the present embodiment, the doubly bend surface of the present invention is not limited to the toroidal surface, and may be an ellipsoid of revolution, a logarithmic spiral surface of revolution, or the like.

According to the manufacturing method of the ninth embodiment, the glass plate 3 is sandwiched between the doubly curved convex surface 21a and the doubly curved concave surface 22a that matches the doubly curved convex surface 21a, and heated to a temperature of 400° C. to 600° C. to be deformed into a shape having the doubly bent surface. As a result, the glass plate 3 is not adversely affected by the surface roughness of the doubly curved convex surface 21a of the convex forming die 21, and has the surface roughness equivalent to that of the glass plate 3 before being heated and deformed. Then, the synthetic multilayer 15 is formed on the concave surface 3a of the glass plate 3. Therefore, it is possible to easily and inexpensively manufacture the doubly bent X-ray spectroscopic device 11 having excellent focusing performance and spectroscopic performance.

Figure 11:
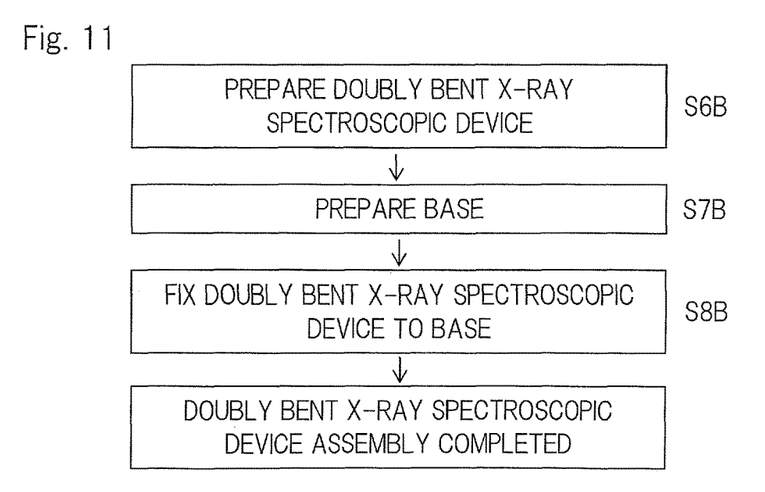
FIG. 11 is a diagram showing process steps of a doubly bent X-ray spectroscopic device assembly manufacturing method according to a tenth embodiment of the present invention.

Next, a method for manufacturing the doubly bent X-ray spectroscopic device assembly 16 according to a tenth embodiment of the present invention will be described. As shown in FIG. 11, this manufacturing method includes: step S6B of preparing the doubly bent X-ray spectroscopic device 11 manufactured by the manufacturing method of the ninth embodiment (FIG. 6); step S7B of preparing the base 7 to which the doubly bent X-ray spectroscopic device 11 is to be fixed; and step S8B of fixing the base 7 to the doubly bent X-ray spectroscopic device 11. Hereinafter, the manufacturing method will be described in order of the process steps.

In step S6B, the doubly bent X-ray spectroscopic device 11 manufactured by the manufacturing method of the ninth embodiment (FIG. 6) is prepared.

In step S7B, the base 7 to which the doubly bent X-ray spectroscopic device 11 is to be fixed is prepared. The same base 7 as that of the doubly bent X-ray focusing device assembly 6 of the second embodiment, for example, a concave stainless-steel base 7 having the same doubly curved concave surface 7a as the doubly curved concave surface 22a of the concave forming die 22, is prepared.

In step S8B, first, an adhesive, for example, epoxy resin, is applied to the entire concave surface 7a of the base 7 (FIG. 2). Next, the convex surface 9 of the doubly bent X-ray spectroscopic device 11 (FIG. 2) is superposed on the concave surface 7a, of the base 7, to which the adhesive is applied. Next, the convex surface 9 of the doubly bent X-ray spectroscopic device 11 is adhered to the concave surface 7a of the base 7 while lightly pressing the doubly bent X-ray spectroscopic device 11 with the doubly curved convex surface 21a of the convex forming die 21. Since the shape of the convex surface 9 of the doubly bent X-ray spectroscopic device 11, which has the self-supporting shape, matches the shape of the concave surface 7a of the base 7, the doubly bent X-ray spectroscopic device 11 is fixed to the base 7 without being deformed. Through the above-described process steps, the doubly bent X-ray spectroscopic device assembly 16 is manufactured.

According to the manufacturing method of the tenth embodiment, since the doubly bent X-ray spectroscopic device 11 manufactured by the manufacturing method of the ninth embodiment is fixed to the base 7, it is possible to easily and inexpensively manufacture the doubly bent X-ray spectroscopic device assembly 16 having excellent focusing performance and spectroscopic performance.

Next, a method for manufacturing the doubly bent X-ray spectroscopic device assembly 16, according to an eleventh embodiment of the present invention will be described. This manufacturing method is different from the manufacturing method of the eighth embodiment only in that, as shown in FIG. 10, step S7D (step on the right side in FIG. 10) of forming the synthetic multilayer 15 which monochromates X-rays, on the concave surface 3a of the glass plate fixed to the base 7 is included instead of step S7C of forming the reflection coating 5 which reflects X-rays, on the concave surface 3a of the glass plate 3 fixed to the base 7, and the other steps are the same as those of the manufacturing method of the eighth embodiment. The synthetic multilayer 15 which monochromates X-rays, for example, a synthetic multilayer for C-Kα line 15, is formed on the concave surface 3a of the glass plate fixed to the base 7, thereby to complete the doubly bent X-ray spectroscopic device assembly 16.

Steps S1 to S6C of the manufacturing method of the eleventh embodiment are the same as steps S1 to S6C of the manufacturing method of the eighth embodiment, and the heated and deformed glass plate 3 is similarly fixed to the base 7.

In step S7D, the synthetic multilayer 15 which monochromates X-rays, for example, a synthetic multilayer 15 for C-Kα line, is formed on the concave surface 3a of the glass plate fixed to the base 7. Through the above-described process steps, the doubly bent X-ray spectroscopic device assembly 16 is manufactured.

According to the manufacturing method of the eleventh embodiment, as in the manufacturing method of the ninth embodiment, the glass plate 3 is sandwiched between the doubly curved convex surface 21a and the doubly curved concave surface 22a that matches the doubly curved convex surface 21a, and heated to a temperature of 400° C. to 600° C. to be deformed into a shape having the doubly bent surface. As a result, the glass plate 3 is not adversely affected by the surface roughness of the doubly curved convex surface 21a of the convex forming die 21, and has the surface roughness equivalent to that of the glass plate 3 before being heated and deformed. Then, the synthetic multilayer 15 is formed on the concave surface 3a of the glass plate 3. Therefore, it is possible to easily and inexpensively manufacture the doubly bent X-ray spectroscopic device assembly 16 having excellent focusing performance and spectroscopic performance.

Although the present invention has been fully described in connection with the preferred embodiments thereof with reference to the accompanying drawings, those skilled in the art will readily conceive numerous changes and modifications within the framework of obviousness upon the reading of the specification herein presented of the present invention. Accordingly, such changes and modifications are, unless they depart from the scope of the present invention as delivered from the claims annexed hereto, to be construed as included therein.

REFERENCE NUMERALS

1 . . . doubly bent X-ray focusing device
3 . . . glass plate
3a . . . concave surface of glass plate
5 . . . reflection coating
6 . . . doubly bent X-ray focusing device assembly
7 . . . base
9 . . . convex surface
11 . . . doubly bent X-ray spectroscopic device
15 . . . synthetic multilayer
16 . . . doubly bent X-ray spectroscopic device assembly
21 . . . convex forming die
21a . . . doubly curved convex surface
22 . . . concave forming die
22a . . . doubly curved concave surface
51 . . . X-ray source
52 . . . primary X-rays
53 . . . sample
54 . . . fluorescent X-rays
56 . . . monochromated fluorescent X-rays
57 . . . X-ray detector

What is claimed is:

1. A method for manufacturing a doubly bent X-ray focusing device, comprising the steps of:
preparing a glass plate having a surface roughness not more than 0.5 nm in root-mean-square roughness;
preparing a convex forming die having a doubly curved convex surface;
preparing a concave forming die having a doubly curved concave surface that matches the doubly curved convex surface;
deforming the glass plate into a shape having a doubly bent surface by sandwiching the glass plate between the doubly curved convex surface of the convex forming die and the doubly curved concave surface of the concave forming die, and heating the glass plate to a temperature of 400° C. to 600° C.; and
forming a reflection coating that reflects X-rays, on a concave surface of the deformed glass plate.

2. A method for manufacturing a doubly bent X-ray focusing device assembly, comprising the steps of:
preparing a doubly bent X-ray focusing device manufactured by the manufacturing method as claimed in claim 1;
preparing a base to which the doubly bent X-ray focusing device is to be fixed; and
fixing the doubly bent X-ray focusing device to the base.

3. A method for manufacturing a doubly bent X-ray focusing device assembly, comprising the steps of:
preparing a glass plate having a surface roughness not more than 0.5 nm in root-mean-square roughness;
preparing a convex forming die having a doubly curved convex surface;
preparing a concave forming die having a doubly curved concave surface that matches the doubly curved convex surface;
deforming the glass plate into a shape having a doubly bent surface by sandwiching the glass plate between the doubly curved convex surface of the convex forming die and the doubly curved concave surface of the concave forming die, and heating the glass plate to a temperature of 400° C. to 600° C.;
preparing a base to which the deformed glass plate is to be fixed;
fixing the deformed glass plate to the base; and
forming a reflection coating that reflects X-rays, on a concave surface of the glass plate fixed to the base.

4. A method for manufacturing a doubly bent X-ray spectroscopic device, comprising the steps of:
preparing a glass plate having a surface roughness not more than 0.5 nm in root-mean-square roughness;
preparing a convex forming die having a doubly curved convex surface;
preparing a concave forming die having a doubly curved concave surface that matches the doubly curved convex surface;
deforming the glass plate into a shape having a doubly bent surface by sandwiching the glass plate between the doubly curved convex surface of the convex forming die and the doubly curved concave surface of the concave forming die, and heating the glass plate to a temperature of 400° C. to 600° C.; and
forming a synthetic multilayer that monochromates X-rays, on a concave surface of the deformed glass plate.

5. A method for manufacturing a doubly bent X-ray spectroscopic device assembly, comprising the steps of:
preparing a doubly bent X-ray spectroscopic device manufactured by the manufacturing method as claimed in claim 4;
preparing a base to which the doubly bent X-ray spectroscopic device is to be fixed; and fixing the doubly bent X-ray spectroscopic device to the base.

6. A method for manufacturing a doubly bent X-ray spectroscopic device assembly, comprising the steps of:

preparing a glass plate having a surface roughness not more than 0.5 nm in root-mean-square roughness;

preparing a convex forming die having a doubly curved convex surface;

preparing a concave forming die having a doubly curved concave surface that matches the doubly curved convex surface;

deforming the glass plate into a shape having a doubly bent surface by sandwiching the glass plate between the doubly curved convex surface of the convex forming die and the doubly curved concave surface of the concave forming die, and heating the glass plate to a temperature of 400° C. to 600° C.;

preparing a base to which the deformed glass plate is to be fixed;

fixing the deformed glass plate to the base; and forming a synthetic multilayer that monochromates X-rays, on a concave surface of the glass plate fixed to the base.

* * * * *